United States Patent [19]
Levin

[11] Patent Number: 5,676,635
[45] Date of Patent: Oct. 14, 1997

[54] INSTRUMENT FOR INSERTION OF AN ENDOTRACHEAL TUBE

[76] Inventor: Bruce Levin, One Independence Pla., Suite 1908, Philadelphia, Pa. 19106

[21] Appl. No.: 522,009

[22] Filed: Aug. 30, 1995

[51] Int. Cl.$^6$ .................................................. A61B 1/267
[52] U.S. Cl. ........................... 600/120; 600/144; 600/146; 600/188
[58] Field of Search ................... 600/146, 153, 600/156–159, 179, 185, 187–188, 199, 120, 157, 144, 143

[56] References Cited

U.S. PATENT DOCUMENTS

| | | | |
|---|---|---|---|
| 3,593,706 | 7/1971 | Schubert . | |
| 3,766,909 | 10/1973 | Ozbey | 600/199 X |
| 3,799,150 | 3/1974 | Bennet . | |
| 3,881,468 | 5/1975 | Foltz . | |
| 4,037,588 | 7/1977 | Heckele . | |
| 4,063,796 | 12/1977 | Hiltebrandt | 350/70 |
| 4,146,019 | 3/1979 | Bass et al. | 600/156 X |
| 4,254,762 | 3/1981 | Yoon | 600/114 |
| 4,335,713 | 6/1982 | Komiya | 128/9 |
| 4,593,682 | 6/1986 | Heckele | 128/6 |
| 4,667,656 | 5/1987 | Yabe | 600/157 X |
| 4,737,142 | 4/1988 | Heckele | 604/95 |
| 4,830,458 | 5/1989 | Hiltebrandt | 350/96.22 |
| 4,846,153 | 7/1989 | Berci | 600/156 X |
| 4,941,457 | 7/1990 | Hasegawa | 128/6 |
| 5,016,614 | 5/1991 | MacAllister | 600/156 X |
| 5,025,778 | 6/1991 | Silverstein et al. | 600/104 |
| 5,046,816 | 9/1991 | Lehmann et al. . | |
| 5,203,320 | 4/1993 | Augustine | 600/187 |
| 5,275,151 | 1/1994 | Shockey et al. | 600/146 X |
| 5,327,881 | 7/1994 | Greene | 600/120 |
| 5,347,992 | 9/1994 | Pearlman et al. | 600/159 X |
| 5,394,865 | 3/1995 | Salerno . | |
| 5,431,152 | 7/1995 | Flam et al. | 600/156 X |

FOREIGN PATENT DOCUMENTS

| | | | |
|---|---|---|---|
| 9112044 | 8/1991 | WIPO | 600/120 |

OTHER PUBLICATIONS

Advertisement from technical journal for "Fiber Optic Laryngoscope" (prior art, date unknown).

*Anesthesiology Product News*, vol. 1, No. 1, pp. 3–4, 11–12 (prior art, date unknown).

Jonathan L. Benumof, M.D., "Management of the Difficult Airway: The ASA Algorithm", pp. 1–7 with 2 drawing pages, 45th Annual Refresher Course Lectures and Clinical Update Program, Annual Meeting of the American Society of Anesthesiologists, Oct. 1994.

Jonathan L. Benumof, M.D., "Management of the Difficult Adult Airway", Medical Intelligence Article, *Anesthesiology*, V 75, No. 6, Dec. 1991, pp. 1087–1109.

*Primary Examiner*—Richard J. Apley
*Assistant Examiner*—John P. Leubecker
*Attorney, Agent, or Firm*—Panitch Schwarze Jacobs & Nadel, P.C.

[57] ABSTRACT

An endotracheal tube insertion system includes a formable shaft having sufficient stiffness to hold a formed shape and having a plurality of longitudinally extending passageways defined therethrough. The instrument further includes a housing connected to the first end of the formable shaft. An image guide cable is disposed in a first longitudinally extending passageway and is optically connected to an eyepiece which is affixed to the first end of the housing. A light source is attached to the second end of the formable shaft proximate the second end of the image guide cable. A baffle member is attached to the second end of the formable shaft proximate to a second longitudinally extending passageway and has an opening directed toward the first longitudinally extending passageway. A fluid port is in fluid communication with the second passageway. A suction port is also provided in fluid communication with a third longitudinally extending passageway. A control line, having one end affixed to the second end of the formable shaft, is slidably disposed in a fourth longitudinally extending passageway for controlling the curvature of the formable shaft.

16 Claims, 2 Drawing Sheets

U.S. Patent    Oct. 14, 1997    Sheet 1 of 2    5,676,635
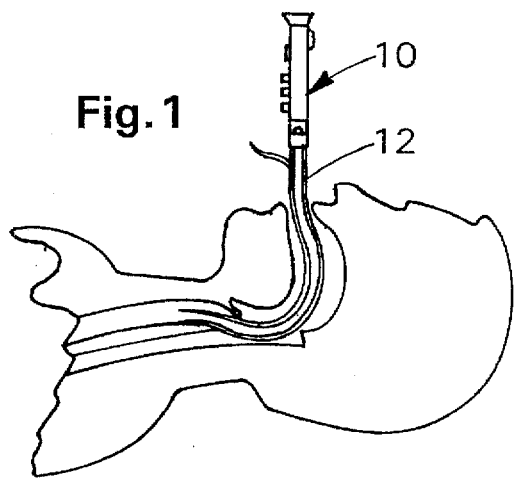
Fig. 1
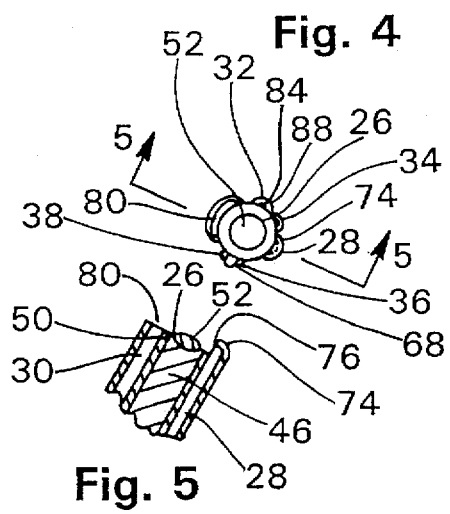
Fig. 4
Fig. 5
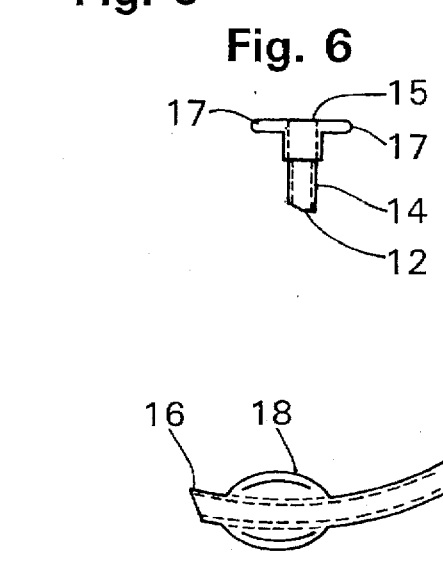
Fig. 3
Fig. 6
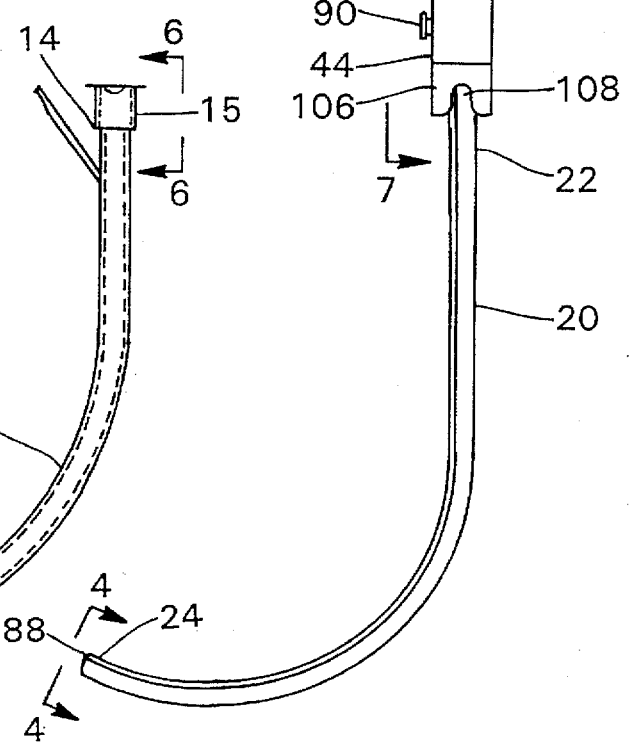
Fig. 2

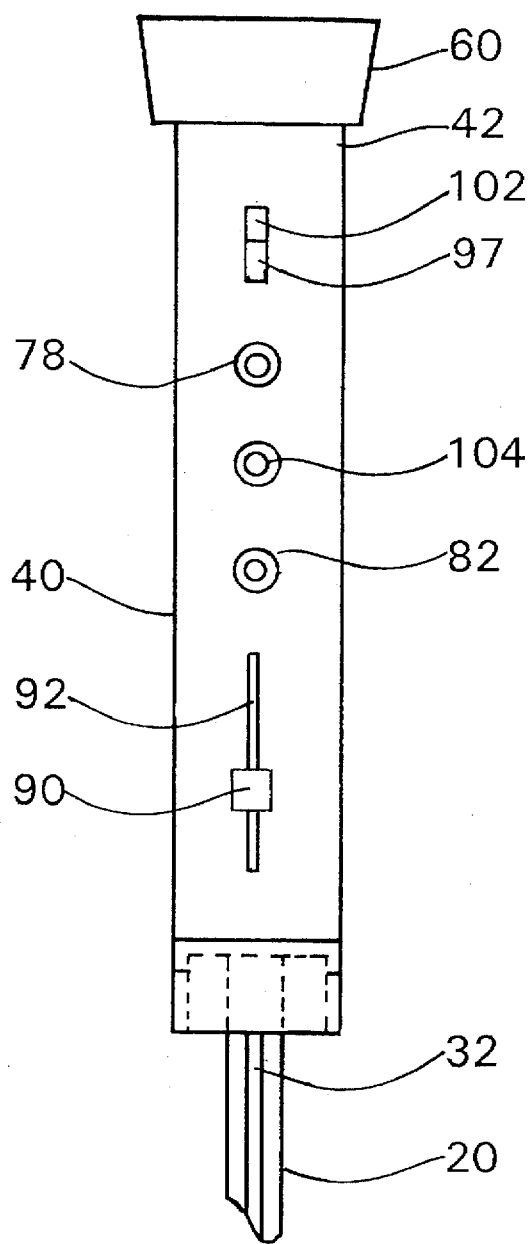
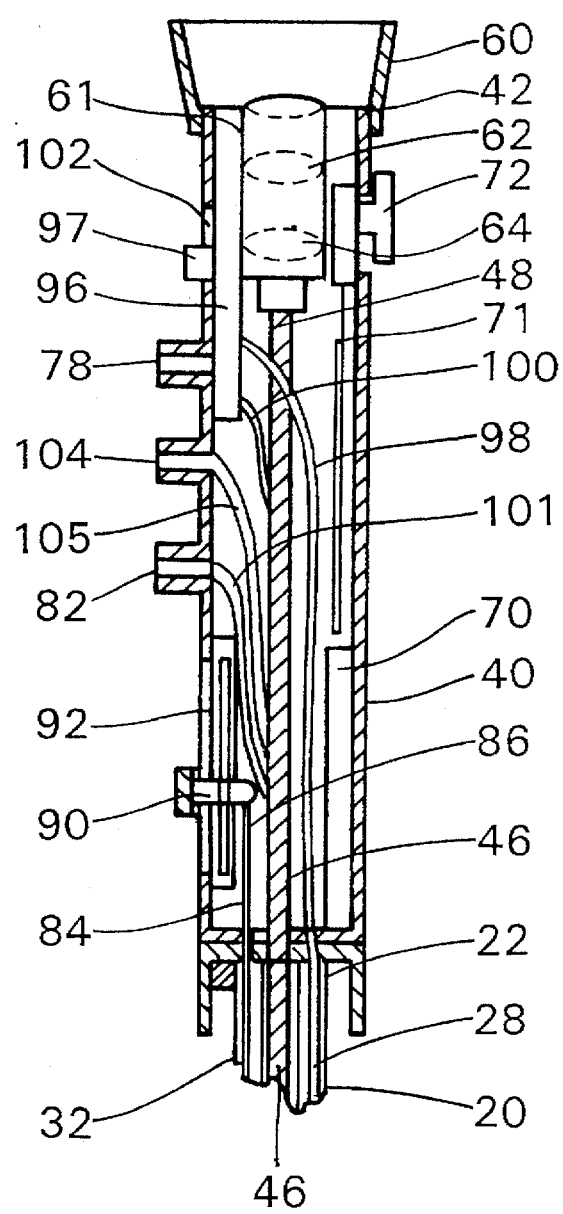
Fig. 7
Fig. 8

INSTRUMENT FOR INSERTION OF AN ENDOTRACHEAL TUBE

FIELD OF THE INVENTION

The present invention relates to an instrument or stylet for insertion of an endotracheal tube. More particularly, the present invention provides an optical stylet for insertion of an endotracheal tube, with the optical stylet having an imaging system to allow a user to accurately guide the instrument during insertion of the endotracheal tube.

BACKGROUND OF THE INVENTION

Endotracheal tubes are typically inserted into patients to provide a patent and protected breathing passage when a patient is unconscious, paralyzed, critically ill and requiring mechanical ventilation or has sustained an injury or trauma which could result in swelling or other obstruction of the airway. Laryngoscopes and bronchoscopes having fiber-optic imaging to facilitate rapid visualization of the larynx are known in the art.

One common prior art method utilizes a laryngoscope held in one hand of the operator. The blade of the laryngoscope displaces the tongue and other tissue allowing the operator to directly visualize the entrance to the larynx. The endotracheal tube, held by the other hand of the operator, is then placed into the trachea. Often a malleable metallic stylet is utilized to allow easier insertion of the endotracheal tube by forming the stylet (and hence the tube carried on the stylet) to the proper shape or contour for insertion. Because of numerous intervening factors, visualization may be impossible and repeated attempts at laryngoscopy may be dangerous. Optimal patient positioning is not always possible in many settings, and this renders laryngoscopy less effective. Furthermore, there are many patient related conditions which may limit the effectiveness of this technique, including the inability to tilt the patient's head to the proper orientation, the inability to open the patient's mouth sufficiently wide, the presence of buck teeth, a floppy epiglottis, anterior glottic orientation, and broken bones in the face or jaw, among others. Any of these can contribute to the inability to secure a patient's airway. This can and does result in death or significant morbidity in the operating suite, emergency room and elsewhere.

Another known intubating system utilizes a laryngoscope having fiber optic imaging and a light source which are fitted on the end of a rigid blade. With practice, the user can visualize the trachea and larynx area through an eyepiece provided on the laryngoscope. A thin metal stylet is attached to the laryngoscope to allow the endotracheal tube to be inserted into the larynx. This system has not met with wide approval for several reasons. The overall system is bulky and not easy for the operator to place into and manipulate within the patient's mouth. The point of visualization is at the end of the rigid blade, not at the end of the endotracheal tube. Thus, the endotracheal tube or other structures may often obscure the necessary view. Additionally, the stylet is not adjustable once in place, making it technically difficult to guide the endotracheal tube into the larynx, even with optimum visualization.

Another known methodology provides a flexible bronchoscope that allows the endotracheal tube to be directed into the trachea under direct visualization. Only the tip of the bronchoscope can be reliably controlled by the operator as it is advanced. This genre of device was initially developed from a diagnostic tool and has not proved useful in many emergency settings. Conceptually, it is problematic to push a loose, cable-like instrument over and around tissue structures which statically or dynamically deflect it. Thus the bronchoscope often curls and may even double back on itself making visualization futile and advancement impossible.

Recently, a stylet has been provided with a lighted distal end. Light is provided by a bulb located at the distal end of the stylet and wires provide current to the bulb. Power is provided by batteries located in the body located at the proximal end of the stylet. The endotracheal tube is installed over the stylet, and the endotracheal tube/stylet are inserted through the patient's mouth toward the glottis. In a dimly lit or dark room, the operator observes the lighted distal end of the stylet shining through the skin of the patient's neck and thorax as the stylet/endotracheal tube are inserted into the proper position in the trachea. This is done without direct visualization of patient anatomy.

The present invention is a result of observation of the limitations with the known prior art devices. These limitations are well documented in the emergency room and anesthesia literature and have very real clinical implications. See Jonathan L. Benumof, M.D., *Management of the Difficult Airway*, 75 Anesthesiology 1087–1110, 1991; Jonathan L. Benumof, M.D., *Management of the Difficult Airway: The ASA Algorithm*, 45th Annual Refresher Course Lectures and Clinical Update Program, American Society of Anesthesiologists, Oct. 15–19, 1994.

The present invention provides a new and significant improvement in the approach to managing the difficult airway.

SUMMARY OF THE INVENTION

Briefly stated, the present invention provides an instrument for insertion of an endotracheal tube into a patient. The instrument comprises a formable shaft having first and second ends, and a plurality of longitudinally extending passageways defined therethrough. The instrument further includes a housing having first and second ends, with the second end of the housing being connected to the first end of the formable shaft. An image guide cable having a first end and a second end is also provided. The image guide cable is disposed in a first longitudinally extending passageway of the shaft. An eyepiece is affixed to the first end of the housing and optics associated with the eyepiece are provided in the housing. The optics are optically connected with the first end of the image guide cable. A light source is attached to the second end of the formable shaft proximate the second end of the image guide cable. A baffle member is attached to the second end of the formable shaft proximate to a second longitudinally extending passageway. The baffle member has an opening directed toward the first longitudinally extending passageway. A fluid port is located on the housing. The fluid port is in fluid communication with the second passageway. A first opening is provided in communication with a third longitudinally extending passageway in the formable shaft. The first opening is located on the second end of the formable shaft on an opposite side of the first passageway from the baffle member. A suction port is also provided located on the housing. The suction port is in fluid communication with the third passageway.

BRIEF DESCRIPTION OF THE DRAWINGS

The foregoing summary, as well as the following detailed description of the preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings:

FIG. 1 is a side elevational view illustrating a preferred embodiment of an instrument for insertion of an endotracheal tube in use in accordance with the present invention;

FIG. 2 is an enlarged side elevational view of the instrument shown in FIG. 1;

FIG. 3 is an enlarged side elevational view of an endotracheal tube which may be intubated utilizing the instrument shown in FIG. 1;

FIG. 4 is an enlarged sectional view taken along line 4—4 in FIG. 2;

FIG. 5 is a section view taken along line 5—5 in FIG. 4;

FIG. 6 is a fragmentary view taken along line 6—6 in FIG. 3;

FIG. 7 is an enlarged fragmentary view taken along line 7—7 in FIG. 2; and

FIG. 8 is a section view taken along line 8—8 in FIG. 7.

DETAILED DESCRIPTION OF THE PREFERRED EMBODIMENT

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the instrument for insertion of an endotracheal tube and designated parts thereof. The terminology includes the words above specifically mentioned, derivatives thereof and words of similar import.

Referring to the drawings, wherein like numerals indicate like elements throughout, there is shown in FIGS. 1–8 a preferred embodiment of an intubating instrument (generally designated 10) for insertion of a tube into a patient in accordance with the present invention. In the preferred embodiment, the intubating instrument 10 is preferably an intubating stylet for insertion of an endotracheal tube as shown in FIG. 1. The instrument 10 is preferably used for insertion of an endotracheal tube 12 through the glottis and into the trachea of a patient. However, those of ordinary skill in the art will recognize that the instrument 10 can be used in other applications.

Referring now to FIG. 2, the instrument 10 comprises a formable shaft 20 having first and second ends 22 and 24, respectively. As shown in FIGS. 4 and 5, a plurality of longitudinally extending passageways 26, 28, 30, 32, 34 and 36 are defined through and are spaced around the formable shaft 20. A housing 40 having first and second ends 42 and 44 is also provided. The second end 44 of the housing 40 is connected to the first end 22 of the formable shaft 20.

In the preferred embodiment, the formable shaft 20 is made of a polymeric material, and has sufficient stiffness to generally hold its form, but yet is soft and formable enough to facilitate insertion into a patient's throat. Preferably, the formable shaft 20 includes first, second, third, fourth, fifth, sixth and seventh longitudinally extending passageways 26, 28, 30, 32, 34, 36 and 38. However, it is understood by those of ordinary skill in the art from the present disclosure that the formable shaft 20 may be made of other materials, such as stainless steel, or a combination of materials, such as a metal base material with a polymeric or plastic coating, if desired. Additionally, it is similarly understood that the number of passageways can be varied, if desired, depending upon the particular application.

In the preferred embodiment, the housing 40 is also made of a polymeric material such as polyvinyl chloride and is generally tubular in form. However, it is understood by those of ordinary skill in the art from the present disclosure that the housing 40 can be made of other materials, such as stainless steel or other suitable materials. Additionally, the shape of the housing 40 may be varied, if desired. For example, the housing 40 could be in the form of a parallelepiped.

Referring to FIGS. 4, 5 and 8, an image guide cable 46 having a first end 48 (FIG. 8) and a second end 50 is disposed in a first longitudinally extending passageway 26 of the formable shaft 20. Preferably, the image guide cable 46 is a fiber optic cable and preferably, the first passageway 26 is proximate the center of the formable shaft 20. However, it will be recognized by those of ordinary skill in the art from the present disclosure that the image guide cable can be located in any position along the formable shaft 20, and is not required to be in a centered location.

Referring now to FIGS. 4 and 5, preferably a wide-angle lens 52 having a predetermined diameter is disposed on the second end 24 of the formable shaft 20. The wide angle lens 52 is optically connected to the second end 50 of the image guide cable 46. The wide angle lens 52 provides a wide angle view from the second, distal end 24 of the formable shaft 20. However, those of ordinary skill in the art will recognize that any type of lens may be optically connected to the second end 50 of the image guide cable 46 on the second end 24 of the formable shaft 20 in accordance with the present invention, depending on the field of vision and magnification desired. Those of ordinary skill in the art will also recognize that the lens 52 on the second, distal end 24 of the formable shaft 20 may be omitted, depending on the particular application.

Referring now to FIGS. 2, 7 and 8, an eyepiece 60 is affixed to the first end 42 of the housing 40. As shown in FIG. 8, the optics associated with the eyepiece 60 are located in an optics tube 61 within the housing 40 below the eyepiece 60. The optics comprise objective lenses 62 and 64, which are optically connected with the first end 48 of the image guide cable 46. Preferably, the objective lenses 62 and 64 are selected such that the optics have an eye relief of approximately 3 to 15 inches. However, it will be appreciated by those of ordinary skill in the art that the focal lengths of the objective lenses 62 and 64 may be such that the eye relief is less than 3 inches, if desired. It will also be appreciated by those of ordinary skill in the art that the number of objective or other lenses used may be varied, depending on the focal length and magnification desired. Preferably, the objective lenses 62 and 64 are axially aligned with the longitudinal axis of the housing 40. However, it will be appreciated by those of ordinary skill in the art that the eyepiece 60 may be located adjacent to one side of the housing 40 on a separate tube (not shown), or the optics tube 61 and eyepiece 60 may be mounted for pivotal movement on the housing 40, if desired.

Referring again to FIGS. 4 and 5, preferably a light source 68 is attached to the second, distal end 24 of the formable shaft 20 proximate the second end 50 of the image guide cable 46. In the preferred embodiment, the light source 68 is provided by a fiber optic light guide which extends through the seventh longitudinally extending passageway 38 of the formable shaft 20. Light is provided to the fiber light guide by a light emitting diode (LED) or incandescent bulb (not shown) located in the housing 40. As shown in FIG. 8, the incandescent bulb or LED is powered by a battery pack 70 which is electrically connected to the LED or incandescent bulb by wires 71, connected in series with a switch 72 for turning the light source 68 off or on. It will be recognized by those or ordinary skill in the art from the present disclosure that the light source 68 could also be provided by an LED or incandescent bulb located at the second, distal end 24 of the formable shaft 20, with wires 71 from the battery pack 70 and switch 72 passing through a passageway in the formable shaft 20.

Referring again to FIGS. 4 and 5, a baffle member 74 is attached to the second, distal end 24 of the formable shaft 20 proximate to the second longitudinally extending passageway 28. The baffle member 74 has an opening 76 which is directed toward the first longitudinally extending passageway 26. As shown in FIGS. 2, 7 and 8, a fluid port 78 for a fluid such as oxygen is located on the housing 40. The fluid port 78 is in fluid communication with the second passageway 28 through a first tube 98 to provide oxygen to the second passageway 28. The oxygen or other fluid exits the second passageway 28 through the opening 76, which is directed toward the first longitudinally extending passageway 26, over the surface of the wide angle lens 52 to clear fluids or other matter from the surface of the wide angle lens 52 for better viewing. When the wide angle lens 52 is not utilized, the opening 76 is directed over the second end 50 of the image guide cable 46 located in the first longitudinally extending passageway 26 to clear the second end 50 of the image guide cable 46 to provide better viewing.

Referring again to FIGS. 4 and 5, a second opening 80 is located on the second end 24 of the formable shaft 20 on an opposite side of the first passageway 26 from the baffle member 74. The second opening 80 is in communication with the third longitudinally extending passageway 30. As shown in FIGS. 2, 7 and 8, a suction port 82 is located on the housing 40. The suction port 82 is in fluid communication with the third passageway 30, preferably through a third tube 101. Suction may be provided through the second opening 80 on the second, distal end 24 of the formable shaft 20, to clear fluid or other matter from the second, distal end 24 of the formable shaft 20. In the preferred embodiment, the second opening 80 has a width which is sufficient to clear the wide angle lens 52. When used in combination with a flow of oxygen or other fluid through the fluid port 78 and the first opening 76, providing the second opening 80 with a width which is equal to at least 30% of the diameter of the wide angle lens 52 should provide adequate cleaning for the lens 52. If a wide angle lens 52 is not utilized, it is preferred that the width of the second opening 76 in communication with the third passageway 30 have a width that is approximately equal to the diameter of the image guide cable 46 to provide good cleaning of the second, distal end 50 of the image guide cable 46. However, those of ordinary skill in the art will appreciate that the size of the second opening 80 may be varied, if desired. For example, the second opening 80 could be smaller if a second baffle member (not shown) were utilized to control the direction of the suction draw. Additionally, the size of the second opening 80 can be varied in inverse proportion to the size of the first opening 76 to achieve sufficient cleaning of the second, distal end 24 of the formable shaft 20.

Referring again to FIGS. 2, 4 and 8, in the preferred embodiment the instrument 10 further comprises a control line 84 having first and second ends 86 and 88, respectively. The control line 84 is slidably disposed in the fourth longitudinally extending passageway 32. The second end 88 of the control line 84 is affixed to the second end 24 of the formable shaft 20 by a mechanical fastener, an adhesive or deformation of fourth passageway 32 adjacent to the second end 24 of the formable shaft 20. As shown in FIGS. 7 and 8, the first end 86 of the control line 84 extends from the first end 22 of the formable shaft 20 into the housing 40. The first end 86 of the control line 84 is attached to a slide member 90 which is slidably disposed in a slot 92 in the housing 40. Movement of the slide member 90 causes the control line 84 to push or pull on the second end 24 of the formable shaft 20, bending the formable shaft 20 to change the curvature of the formable shaft 20 during use. This allows the user to more easily insert the formable shaft 20 into the patient's tracheal tube without necessarily having to withdraw the instrument 10 from the patient's throat during the procedure to manually bend or form the formable shaft 20.

Referring to FIG. 8, a valve 96, which is preferably a 3-way valve, is located inside the housing 40. The valve 96 is in fluid communication between the fluid port 78, the second longitudinally extending passageway 28, and the fifth longitudinally extending passageway 34. More particularly, the first tube 98 located in the housing 40 extends between the second passageway 28 and the valve 96 and a second tube 100 extends between the fifth passageway 34 and the valve 96 to provide a connection between the valve 96 and the passageways. The valve 96 includes an actuator 97 which extends through a second slot 102 in the housing 40. The valve 96 is actuatable between a first position, where the fluid port 78 is in fluid communication with the second passageway 28, via the first tube 98, and a second position where the fluid port 78 is in fluid communication with the fifth passageway 34, via the second tube 100. When the valve actuator 97 is in the first position, oxygen or another fluid can be used to clean the surface of the wide angle lens 52, as previously described. When the valve actuator 97 is in the second position, oxygen or another fluid can be directed outward from the second end 24 of the formable shaft 20, to supply oxygen or another fluid directly to the patient, or to clear or probe direct obstructions in the breathing path.

Referring to FIGS. 4, 7 and 8, in the preferred embodiment the instrument 10 further comprises an IV port 104 located on the housing 40. The IV port 104 is in fluid communication with the sixth passageway 36, to allow medicine or other materials to be delivered directly to the patient through the second end 24 of the formable shaft 20. More particularly, the IV port 104 located on the housing 40 is connected by a fourth tube 105 to the sixth passageway 36 at the first end 22 of the formable shaft 20.

Referring to FIGS. 1–3, the tracheal tube 12 is shown in detail. The tracheal tube 12 is slidably disposed on the formable shaft 20 during intubation procedures, as shown in FIG. 1, and has been illustrated separately from the instrument 10 in FIGS. 2 and 3. The tracheal tube 12 is generally made of a clear polymeric material and is of a type generally known to those of ordinary skill in the art. Generally, the tracheal tube 12 has a first end 14 and a second end 16. Generally, a fitting 15 is located on the first end 14 of the tracheal tube 12. As shown in FIGS. 3 and 6, the fitting 15 generally includes a pair of radially outwardly extending arms 17. As shown in FIG. 3, an inflatable bladder 18 may be provided on the second end 16 of the tracheal tube 12. The bladder 18 may be inflated in a manner known to those of ordinary skill in the art after the tracheal tube 12 has been inserted to hold it in position.

In the preferred embodiment, the instrument 10 includes a second fitting 106 attached to the housing 40 adjacent to the first end 22 of the formable shaft 20. The second fitting 106 includes two complementary shaped recesses 108 which are configured to receive the arms 17 to prevent the tracheal tube 12 from being twisted relative to the formable shaft 20 of the instrument 10. Preferably, the second fitting 106 is molded from a polymeric material. However, it is understood by those of ordinary skill in the art from the present disclosure that the second fitting 106 could be made by other methods, such as machining, and the second fitting 106 can be made from other suitable materials, such as stainless steel, if desired.

The instrument 10 may also include a video processor (not shown) in optical communication with the image guide cable 46 to convert the observed image to an electronic video signal. The video signal can then be used to display the image being viewed at the second end 24 of the formable shaft 20 on a monitor (not shown).

In use, the endotracheal tube 12 is placed over the formable shaft 20. Generally, the second end 24 of the shaft 20 extends beyond the second end 16 of the tracheal tube 12 to allow for better viewing through the lens 52. The user holds the housing 40 and inserts the second, distal end 24 of the formable shaft 20 along with the second end 16 of the endotracheal tube 12 into the patient's mouth. The switch 72 is used to turn on the light source 68. The movement of the second, distal end 24 of the formable shaft 20 can be observed through the eyepiece 60. The arrangement of objective lenses 62, 64 is such that the eye relief from the eyepiece 60 is 3 to 15 inches allowing the user to have his eye away from the eyepiece to view the image at the second, distal end 24 of the formable shaft 20 as he manipulates the instrument 10.

An oxygen source (not shown) is be connected to the fluid port 78. The fluid port 78 supplies oxygen through the second or fifth passageways 28 or 34, depending on the position of the actuator 97 for the valve 96. A suction line is connected to the suction port 82. The suction port 82 clears fluid matter from in front of the distal end 24 of the formable shaft 20 by drawing it through the second opening 80 and the third passageway 30. If the wide angle lens 52 becomes obscured with fluid matter (or in the case where the wide angle lens 52 is not utilized, where the second end 50 of the image guide cable 46 becomes obscured), the actuator 97 for the 3-way valve 96 is set in a first position such that the fluid port 78 is in fluid communication with the second passageway 28 via the first tube 98. The flow of oxygen from the second passageway 28 is directed by the baffle member 74 through the first opening 76 across the wide angle lens 52 (or the second end 50 of the image guide cable 46). The flow of oxygen across the wide angle lens 52 clears the fluid matter, allowing the user to again see through the second end 50 of the image guide cable 46. The suction through the third passageway 30 at the second, distal end 24 of the formable shaft 20 also assists in drawing the fluid matter from the wide angle lens 52 (or from the surface of the second end 50 of the image guide cable 46, if used) in combination with the flow of oxygen from the first opening 76.

Once the second, distal end 24 of the formable shaft 20 has been guided through the glottis into the trachea, oxygen can be directed from the fluid port 78 directly into the trachea through the fifth passageway 34 by movement of the valve actuator 97 from the first position, where the fluid port 78 is in fluid communication with the second passageway 28, to the second position where the fluid port 78 is in fluid communication with the fifth passageway 34 via the second tube 100.

If the user has difficulty in inserting the formable shaft 20 through patient's glottis, the slide member 90 can be used to move the control line 84 to adjust the curvature of the formable shaft 20. Furthermore, a standard laryngoscope, as described in the background, can be used to provide soft tissue clearance. Medicine can also be introduced into the patient through the IV port 104.

After the endotracheal tube 12 has been properly located, the instrument 10 can be withdrawn, leaving the endotracheal tube 12 in position.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An endotracheal tube insertion system including an instrument for insertion of an endotracheal tube into a patient comprising:

a formable shaft having sufficient stiffness along the entire length to hold a formed shape, the formable shaft having first and second ends, and a plurality of longitudinally extending passageways defined therethrough;

a housing having first and second ends, the second end of the housing being connected to the first end of the formable shaft;

an image guide cable having a first end, a second end and a predetermined diameter, the image guide cable being disposed in a first longitudinally extending passageway of the shaft;

an eyepiece affixed to the first end of the housing and optics associated with the eyepiece, the optics being optically connected with the first end of the image guide cable;

means for providing light located at the second end of the formable shaft proximate the second end of the image guide cable;

a baffle member attached to the second end of the formable shaft proximate to a second longitudinally extending passageway, the baffle member having a first opening directed toward the first longitudinally extending passageway;

a fluid port located on the housing, the fluid port being in fluid communication with the second passageway;

a second opening located on the second end of the formable shaft on an opposite side of the first passageway from the baffle member, with the baffle member being directed toward the second opening, the second opening being in communication with a third longitudinally extending passageway;

a suction port located on the housing, the suction port being in fluid communication with the third passageway; and a control line having first and second ends slidably disposed in a fourth longitudinally extending passageway, the second end of the control line being affixed to the second end of the formable shaft.

2. The system of claim 1 further comprising a tracheal tube slidably disposed on the formable shaft.

3. The system of claim 1 further comprising a control line having first and second ends slidably disposed in a fourth longitudinally extending passageway, the second end of the control line being affixed to the second end of the formable shaft.

4. The system of claim 1 further comprising a fifth longitudinally extending passageway and a valve in fluid communication between the fluid port, the second longitudinally extending passageway, and the fifth longitudinally extending passageway, the valve being actuatable between a first position, where the fluid port is in fluid communication with the second passageway, and a second position, where the fluid port is in fluid communication with the fifth passageway.

5. The system of claim 1 further comprising a sixth longitudinally extending passageway in the formable shaft and an IV port located on the housing, the IV port being in fluid communication with the sixth passageway.

6. The system of claim 1 wherein a wide angle lens having a diameter is disposed on the second end of the formable shaft, the wide angle lens being optically connected to the second end of the image guide cable.

7. The system of claim 6 wherein the second opening in communication with the third longitudinally extending passageway has a width which is equal to at least 30% of the diameter of the wide angle lens.

8. The system of claim 1 wherein the second opening in communication with the third passageway has a width that is approximately equal to the diameter of the image guide cable.

9. The system of claim 1 wherein the eyepiece and optics provide an eye relief of approximately 3 to 15 inches.

10. An endotracheal tube insertion system including an instrument for insertion of a tracheal tube comprising:

a formable shaft having sufficient stiffness along the entire length to hold a formed shape, the formable shaft having first and second ends, and a plurality of longitudinally extending passageways defined therethrough;

a fiber optic image guide cable having a first end and a second end disposed in a first longitudinally extending passageway;

means for providing light located at the second end of the formable shaft proximate the second end of the fiber optic guide cable;

a baffle member attached to the second end of the formable shaft in proximity to a second longitudinally extending passageway, the baffle member having an opening directed toward the first longitudinally extending passageway;

a second opening in communication with a third longitudinally extending passageway, the second opening being located on the second end of the formable shaft on an opposite side of the first passageway from the baffle member, with the baffle member being directed toward the second opening;

a control line having first and second ends slidably disposed in a fourth longitudinally extending passageway, the second end of the control line being affixed to the second end of the formable shaft;

a housing attached having first and second ends, the second end of the housing being connected to the first end of the formable shaft;

an eyepiece affixed to the first end of the housing and optics associated with the eyepiece, the optics being optically connected with the first end of the fiber optic image guide cable, the eyepiece and optics having an eye relief of approximately 3 to 15 inches;

a fluid port attached to the housing, the fluid port being in fluid communication with the second passageway;

a suction port attached to the housing, the suction port being in fluid communication with the third passageway;

a switch located on the housing, the switch being in electrical communication with the light source; and an actuator member slidably disposed on the housing, the slide member being connected to the first end of the control line.

11. The system of claim 10 further comprising a tracheal tube slidably disposed on the formable shaft.

12. The system of claim 10 further comprising a fifth longitudinally extending passageway and a valve in fluid communication between the fluid port and the second longitudinally extending passageway, the fifth longitudinally extending passageway being in fluid communication with the valve, the valve being actuatable between a first position, where the fluid port is in fluid communication with the second passageway, and a second position, where the fluid port is in fluid communication with the fifth passageway.

13. The system of claim 10 further comprising a sixth longitudinally extending passageway in the formable shaft and an IV port located on the housing, the IV port being in fluid communication with the sixth passageway.

14. The system of claim 10 wherein a wide angle lens is disposed on the second end of the formable shaft, the wide angle lens is optically connected to the second end of the fiber optic image guide cable.

15. The system of claim 14 wherein the width of the opening in communication with the third longitudinally extending passageway has a width which is equal to at least 30% of the diameter of the wide angle lens.

16. The system of claim 10 wherein the opening in communication with the third passageway has a width that is approximately equal to the diameter of the fiber optic image guide cable.

* * * * *